(12) United States Patent
Saul et al.

(10) Patent No.: US 8,101,916 B2
(45) Date of Patent: Jan. 24, 2012

(54) METHOD FOR MEASURING BIODIESEL CONCENTRATION IN A BIODIESEL DIESEL OIL MIXTURE

(75) Inventors: Cyro Ketzer Saul, Curitiba (BR);
Marcelo Adriano Aliske, Mandirituba (BR); Wanderley Veiga, Curitiba (BR)

(73) Assignee: Instituto De Tecnologia Do Parana—Tecpar, Curitiba, Parana (BR)

( * ) Notice: Subject to any disclaimer, the term of this patent is extended or adjusted under 35 U.S.C. 154(b) by 0 days.

(21) Appl. No.: 12/598,290

(22) PCT Filed: Jul. 13, 2007

(86) PCT No.: PCT/BR2007/000182
§ 371 (c)(1),
(2), (4) Date: Oct. 30, 2009

(87) PCT Pub. No.: WO2009/009843
PCT Pub. Date: Jan. 22, 2009

(65) Prior Publication Data
US 2010/0116991 A1    May 13, 2010

(51) Int. Cl.
*G01N 21/35* (2006.01)
(52) U.S. Cl. .................................. 250/339.07
(58) Field of Classification Search ............. 250/339.07; 356/51, 70
See application file for complete search history.

(56) References Cited

U.S. PATENT DOCUMENTS
7,155,334 B1 * 12/2006 Stewart et al. ................ 701/114
2006/0213554 A1   9/2006 Welch et al.

FOREIGN PATENT DOCUMENTS
EP    0 494 734 B1   5/1998
JP    59219598 A     12/1984
WO    WO 90/03565    4/1990

OTHER PUBLICATIONS

Knothe, Gerhard, Determining the Blend Level of Mixtures of Biodiesel with Conventional Diesel Fuel by Fiber-Optic Near-Infrared Spectroscopy and 1H Nuclear Magnetic Resonance Spectroscopy, Paper No. J9859 in JAOCS 78, 1025-1028 (Oct. 2001).*
Boyd et al., Jun. 2007, Simplified Biofuels Measurements with Mid Infrared Analysis, ECO Services International, whole document.*
Ritz et al., Oct. 1, 2004, Mid-Infrared Fuel Analysis, Biodiesel Magazine, whole document.* Aliske et al., 2007, "Measurement of Biodiesel Concentration in a Diesel Oil Mixture", Fuel, vol. 86:1461-1464.
PCT International Search Report, Sep. 20, 2007, for Instituto de Tecnologia Do Parana, Int'l Application No. PCT/BR2007/000182, filed Jul. 13, 2007.
PCT Written Opinion of the International Searching Authority, Sep. 20, 2007, for Instituto de Tecnologia Do Parana, Int'l Application No PCT/BR2007/000182, filed Jul. 13, 2007.

* cited by examiner

*Primary Examiner* — David Porta
*Assistant Examiner* — Marcus Taningco
(74) *Attorney, Agent, or Firm* — Law Offices of Albert Wai-Kit Chan, PLLC

(57) ABSTRACT

This patent presents a method for measuring the concentration of biodiesel in a homogeneous biodiesel-diesel oil mixture using mid infrared radiation for use as fabrication monitor, quality control, law enforcement and multi-fueled vehicles. The method is characterized by the use of mid infrared absorption measurement in the range from 1870 to 1600 $cm^{-1}$ (5347.6 to 6250.0 nm) which corresponds to the carbonyl group absorption peak (C=O) that is only present in biodiesel. Both intensity and area of the carbonyl absorption peak present power law dependence with the biodiesel percentile in the biodiesel-diesel oil mixture.

9 Claims, 4 Drawing Sheets

Single Beam Measurement System

Double Beam Measurement System

METHOD FOR MEASURING BIODIESEL CONCENTRATION IN A BIODIESEL DIESEL OIL MIXTURE

This application is the National Stage of International Application No. PCT/BR2007/000182, filed Jul. 13, 2007. The entire contents and disclosures of the preceding application are incorporated by reference into this application.

DISCLOSURE

The invention herein described relates to a method for measuring the concentration of biodiesel in a homogeneous mixture of biodiesel and diesel oil using infrared radiation.

BACKGROUND OF THE INVENTION

The reduction of pollutant gases in the atmosphere, responsible for global warming, associated with global oil reserves reduction pushed many countries to search for an alternative solution of both problems. Brazil, as one of the pioneers in the use of alternative fuels, mostly due to the development of the ethanol technology, has started an ambitious program regarding Biodiesel. Biodiesel is an organic fuel that can be obtained through different processes, being the transesterification of oil the most commonly used. The oil used in the process can be from animal or vegetal origin or a mixture of both. Since Brazil has one of the biggest cultivable areas in the world, it is evident that the success in the domain of this technology depends mostly of political will. The law 11.097, of Jan. 13, 2005, establishes a mandatory minimum mixture percentile of biodiesel in the diesel oil to be commercialized to the public all over the country. This percentile will be of 5% after eight years after the law publication date, with an intermediary value of 2% three years after the publication. In the future the tendency is to an increase in those percentiles as a function of the increase of global warming and due to global political conjuncture regarding natural oil sources. Based on the presented situation it becomes evident the need for a method to determine mixture percentiles of biodiesel in diesel oil for manufacture control, quality control, law enforcement and for engine managing and control.

The previous art related regards to the mixture measurement of alcohol-gasoline mixture measurements using near infrared light ("Near Infrared" or NIR—0.65 a 2.5 μm).

International patent WO90/03565 of Apr. 5, 1990, titled "Sensor and Method for Measuring Alcohol Concentration in Alcohol-Gasoline Mixture" is related to a sensor and a method to measure mixtures of alcohol-gasoline mixtures for vehicular applications. The sensor delivers the information about the percentile of mixture to the injection system control, allowing the adjustment of fuel-air ratio. The method is based on the use of two different wavelengths, being one of then highly absorbed by alcohol and weakly absorbed by gasoline, and the second equally absorbed by both liquids. While one of the filters is centered at 1550 nm and the other is centered at 1300 nm, although other wavelengths can be used, in the ranges of 1450-1650 nm and in the range of 1200-1400 nm. The light source is an incandescent lamp working below its nominal voltage. The detectors are based on thermocouples suited to operate in the appropriate ranges. This system also comprises filters, to select the specific wavelength ranges, and the necessary electronics to amplify and further process the signals.

European patent EP0494734B1, of Aug. 5, 1998, titled "A method and Apparatus for Determining the Composition of a Fuel Mixture" is related to a method to determine the composition of a fuel mixture as well as the equipment used measure it. This patent is related to the measurement of the mixture o alcohols (ethanol and methanol) with gasoline, as well as the percentile of the many compounds that constitute gasoline. The method consists of absorbance measurement in the near infrared (NIR—between 650 and 2500 nm), more specifically to the stretching motion of the C—H bond located between 2000 and 2500 nm, 1700 and 1800 nm and a small peak at 1200 nm, as well as the stretching of the O—H bond observed between 1400 and 1650 nm. The method uses a double beam for emulsification detection which can happen in alcohol gasoline mixtures. The apparatus is designed to be used embarked allowing the vehicle ignition system to know which proportion of mixture is being injected in the pistons, and therefore allowing adjust the performance of the engine. The apparatus uses a light source which emits radiation in the near infrared range. The light detection is performed using InGaAs detectors which operate in de referred range. Interference filters are used to select the appropriate wavelengths. The apparatus also uses a diode located within the measurement chamber to measure temperature allowing appropriate corrections in the measurements.

SUMMARY OF THE INVENTION

The present invention provides a method for measuring the concentration of biodiesel in biodiesel-diesel oil mixtures from 0% up to 100%, which means all the range. The validity of the present method is confirmed by the existing previous art used to measure alcohol-gasoline mixtures using near infrared.

The method of the present invention consists of measuring the absorbance in the mid infrared range (from 2000 to 909.09 $cm^{-1}$ or 5000 to 11000 nm). Within this range there are many peaks that can be used to perform the mixture percentile measurement, although we found the peak at 1870-1600 $cm^{-1}$ m (5347.6 to 6250.0 nm) the preferred to perform the measurements. According to Silverstein, Bassler and Morril (Spectrometric Identification of Organic Compounds; Wiley: New York, 1991) this peak corresponds to the carbonyl group (C=O) absorption, known as the carbonyl peak, typical of esters. This absorption peak is connected to the stretching vibration of ester groups, and is known by its relatively constant position and freedom from interfering bands. For biodiesel this is the strongest absorption peak in the mid infrared range independently of raw material source and process route (ethylic or methylic). In diesel oil there are no observable absorption peaks within this range.

Therefore the method of the present invention allows a direct measurement o biodiesel percentile in a biodiesel-diesel oil mixture using mid infrared absorption measurement within the carbonyl peak range.

DETAILED DESCRIPTION

Figure 1:
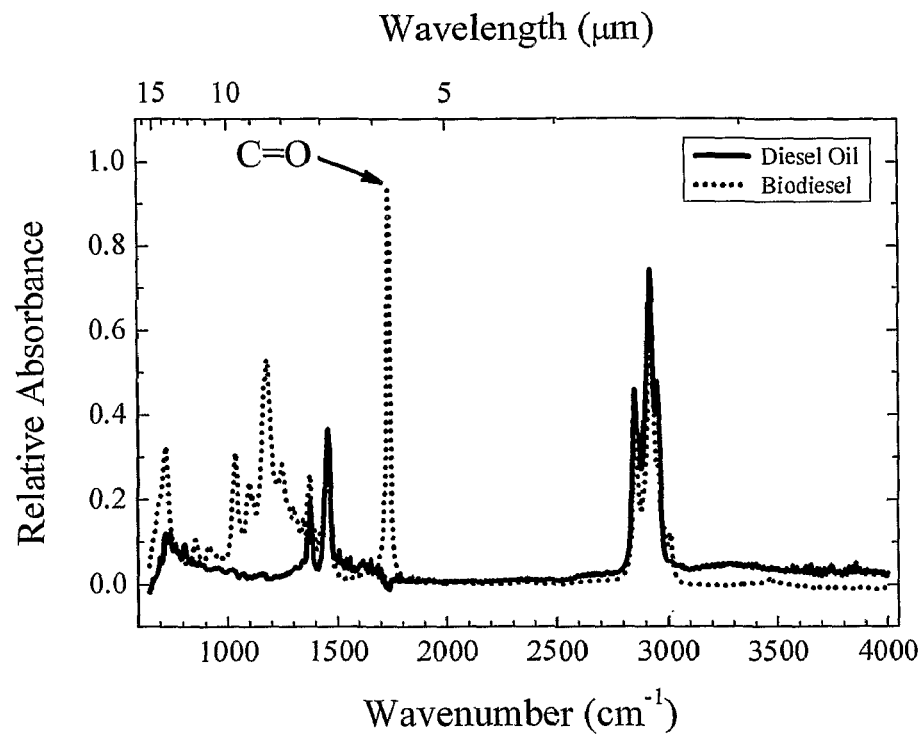
FIG. 1 is a graph of absorbance vs. wave number (wavelength) for a typical biodiesel and diesel oil identifying the carbonyl peak present in the biodiesel spectrum.
Figure 2A:
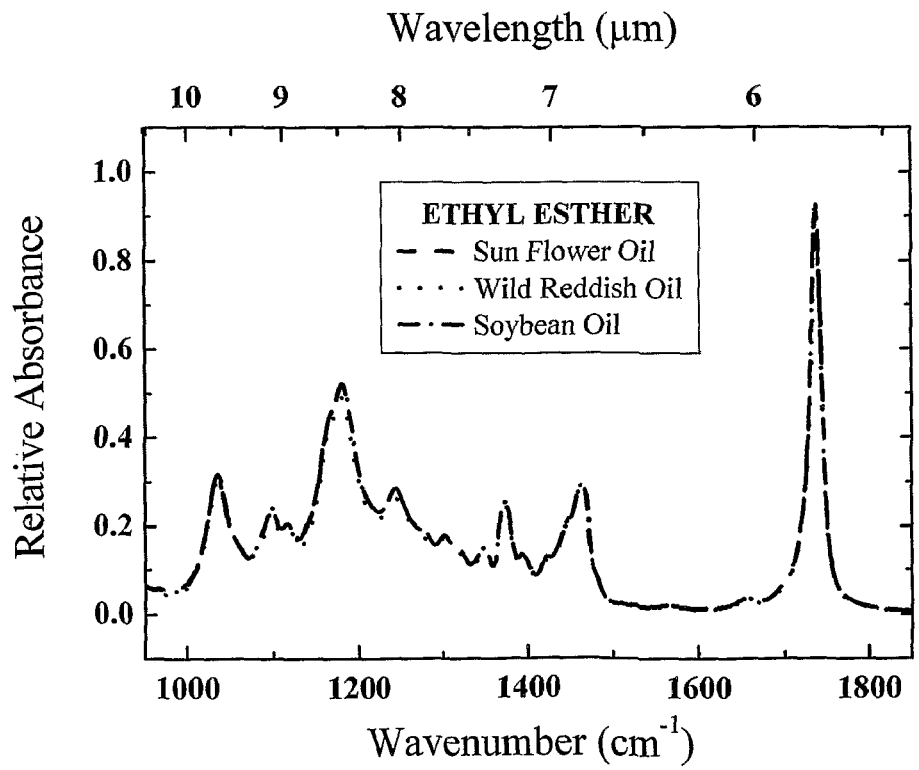
FIGS. 2a and 2b are graphs of absorbance vs. wave number (wavelength) for ethyl ester (ethylic biodiesel) 2a, and for methyl ester (methylic biodiesel) 2b. In both cases the spectra are perfectly superimposed.
Figure 2B:
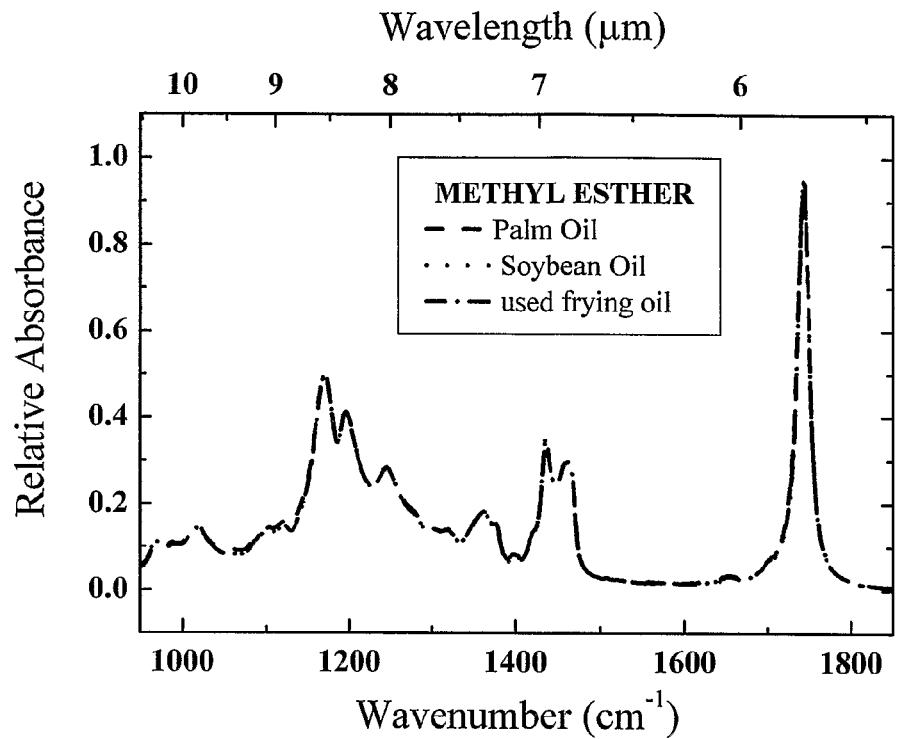
Figure 3:
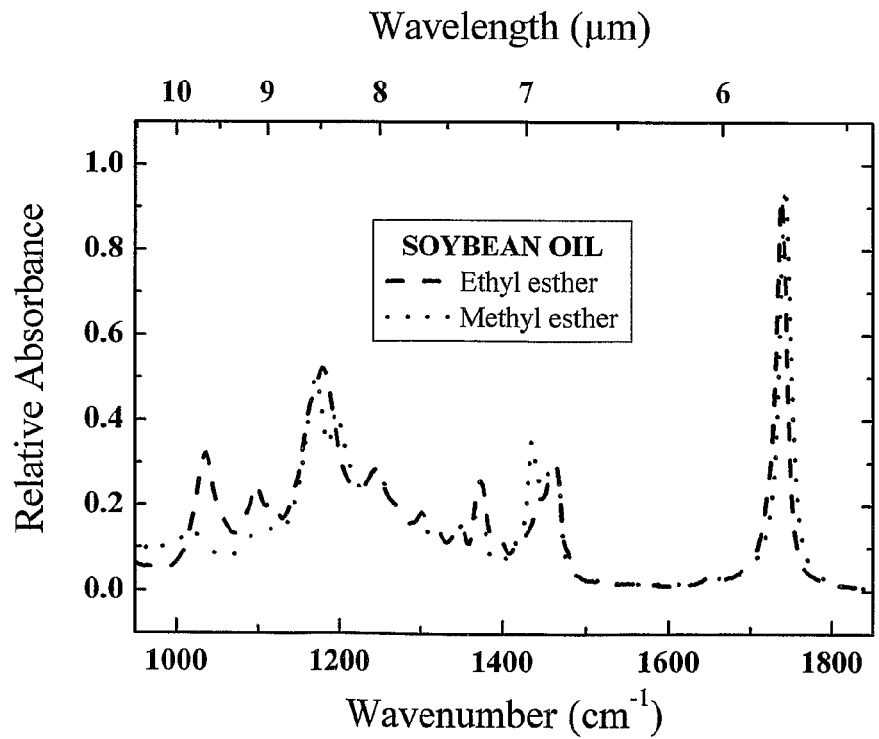
FIG. 3 is a graph of absorbance vs. wave number (wavelength) for ethyl and methyl esters obtained from soybean oil. It is evident that the carbonyl peak presents almost no difference.
Figure 4:
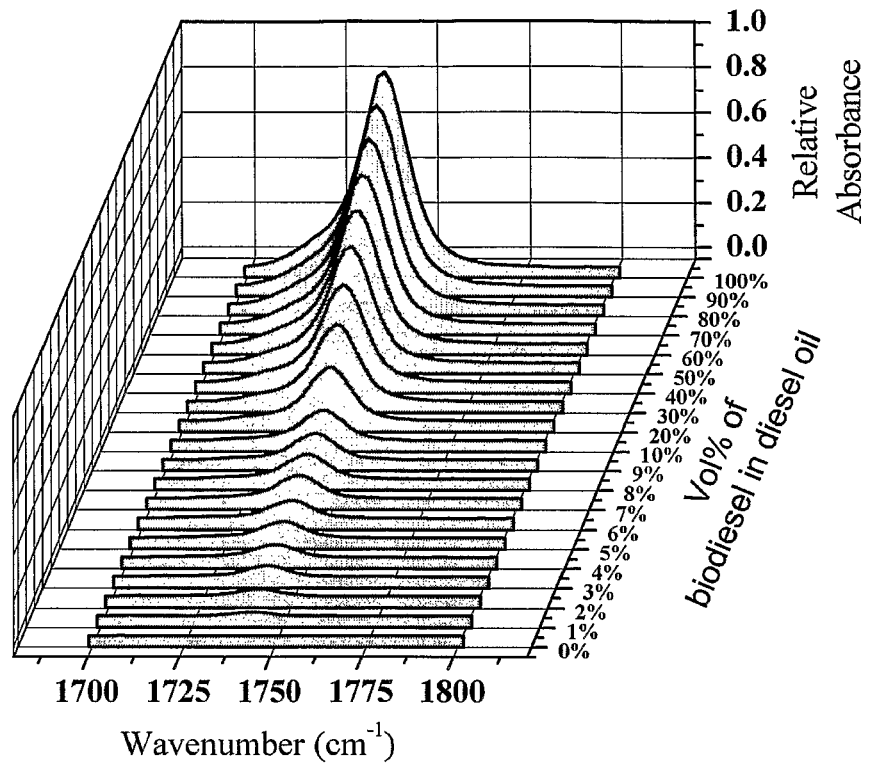
FIG. 4 is a three-dimensional graph of the carbonyl peak (C=O) absorbance vs. wave number (wavelength) vs. biodiesel concentration from 0 to 100%.
Figure 5:
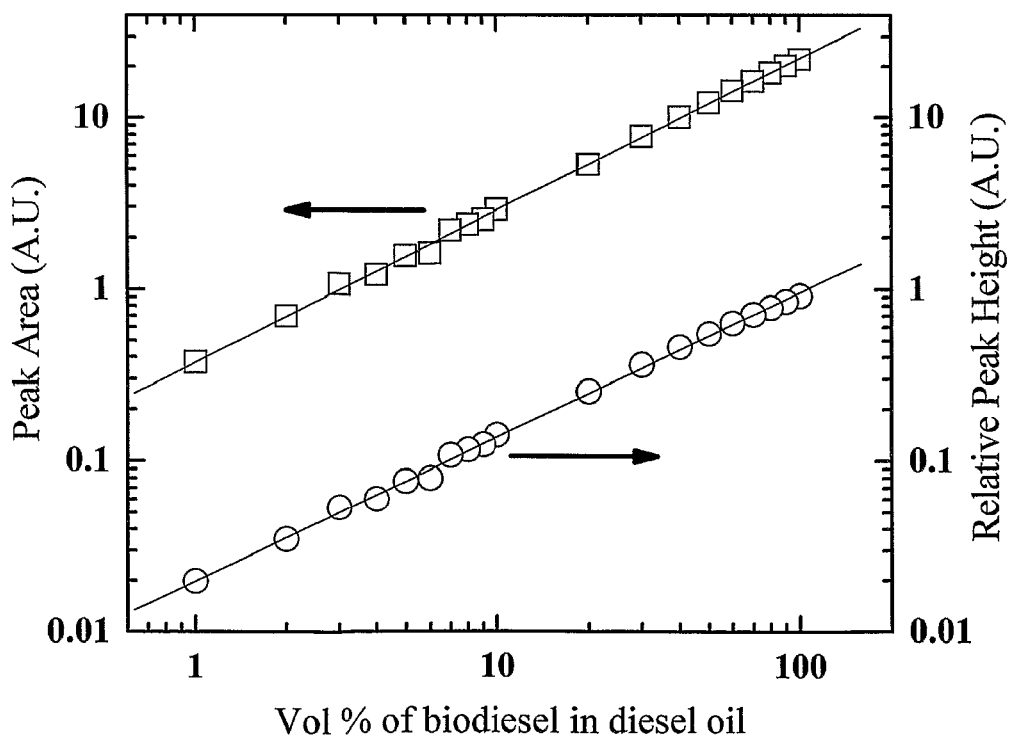
FIG. 5 is a log-log graph for both area and height of the carbonyl peak (C=O) vs. the biodiesel concentration, which shows a clear power law behavior for both parameters.

Regarding the spectra presented in the many graphs it is important to state that all measurements were performed on samples without pre-treatment, which are is the conditions for future applications as quality control. Measurements of absorbance were performed using 32 scans in the range from 4000 to 600 cm$^{-1}$ with a resolution of 4 cm$^{-1}$. The spectra were obtained without baseline corrections. Even the comparisons between different samples were performed using raw data. FIG. 1 shows typical absorption spectra of biodiesel and diesel oil. This graph shows that not only carbonyl peak (C=O) located at 1736 cm$^{-1}$ (5760.4 nm), but also a group of peaks between 1000 and 1300 cm$^{-1}$ (10000 and 7692.3 nm) which are not present in the diesel oil spectrum. This last group of peaks can be used in the process of the mixture percentile measurement, but they present two basic disadvantages when compared to the carbonyl peak. Those peaks are less intense than the carbonyl peak and their relative heights change a little bit with the raw material source and mostly with the process route (ethylic or methylic). FIGS. 2*a* and 2*b* present absorbance spectra for two different process routes to obtain biodiesel, the ethylic route in FIG. 2*a* and the methylic in 2*b*, obtained from different raw materials. No appreciable differences are visible in both graphs and therefore the spectra are almost completely superimposed. The carbonyl peak is always the most prominent indicating its high suitability for the percentile mixture measurement. Slight changes can be observed in the range from 1000 and 1300 cm$^{-1}$ (10000 and 7692.3 nm) mostly for the ethylic route. FIG. 3 presents a comparative graph for two different routes of synthesis of biodiesel starting from soybean oil. For both routes the carbonyl peak is the most prominent and presents almost no change, while the peaks from 1000 and 1300 cm$^{-1}$ (10000 and 7692.3 nm) present variations easily perceptible. Again this evidence strengthens the option for the carbonyl peak as a choice for mixture percentile measurements. FIG. 4 presents a set of graphs of the carbonyl peak obtained at different mixture percentiles and organized to create a three-dimensional graph. For great concentrations of biodiesel the variation step used was 10% and for concentrations below 10% the step used was 1% in order to check the suitability of the method for concentrations to be initially used in Brazil and in other countries. FIG. 5 indicates that the relation between both carbonyl peak area and height with mixture percentile shows a slight non-linear behavior. By plotting the data in a log-log graph it is possible to determine that it presents a power-law behavior. Power laws always appear as straight lines when plotted in log-log graphs. For peak area the behavior can be mathematically described by the equation $$\text{PeakArea}=0.373\times(\text{Vol}\%)^{0.889}, \quad (1)$$

where Vol % represents the volumetric percentile of biodiesel in the biodiesel-diesel oil mixture. Those values are based on the data gathered in our measurements and slight changes in the numeric value of the exponent are expected. The multiplier term can accept bigger changes due to sample turbidity. For peak height the mathematical equation that describes the behavior is $$\text{PeakHeight}=0.0199\times(\text{Vol}\%)^{0.841}, \quad (2)$$

where Vol % represents the volumetric percentile of biodiesel in the biodiesel-diesel oil mixture. As in the previous equation we expect slight changes in the exponent value and bigger changes in the multiplier due to the same reasons. Nowadays this kind of non-linearity presents no problem due to the possibility of analogical or digital processing of the raw signal.

The measurement can be performed in the laboratory, in the field or associated with the vehicle engine management system. In the laboratory the measurement should be preferably measured using Fourier transform spectroscopy (FTIR) preferably centered in the carbonyl peak (C=O) range around 1736 cm$^{-1}$ (5760.4 nm). Field measurements should be preferably performed using portable equipment.

The preferable embodiment for laboratory, field or embarked measurement system should include a mid infrared radiation source, a liquid sample holder a band-pass filter system centered preferably in the carbonyl peak (C=O) range, a detector able to operate in the mid infrared range and a data processing unit able to collect and process the signals to determine the mixture percentile.

Figure 6:
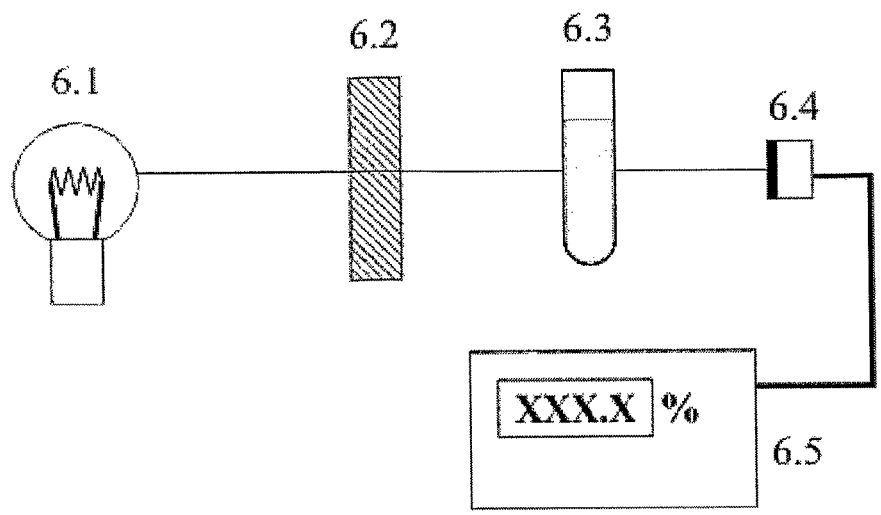
FIG. 6 is simplified schematic diagram of a single beam measurement setup to perform the measurement according to the method presented in this patent. This setup can be adapted for laboratory, field or embarked application.
Figure 7:
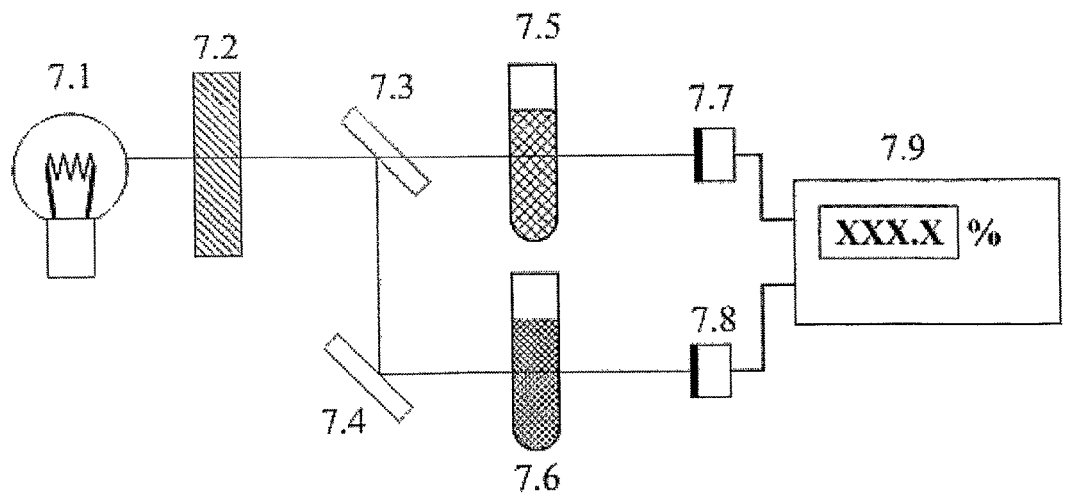
FIG. 7 is simplified schematic diagram of a double beam measurement setup to perform the measurement according to the method presented in this patent. This setup can also be adapted for laboratory, field or embarked application.

FIG. 6 shows a single bean configuration and FIG. 7 shows a double beam configuration. For vehicular applications the measurement system should be preferably installed in the fuel line and the output signal has to be compatible with the vehicle control system. The infrared source should be preferably an incandescent light bulb (6.1 and 7.1) operating below its nominal voltage to maximize the emission near the carbonyl peak range. Interference and absorption filters (6.2 and 7.2) are preferable to insure the elimination of wavelengths outside the carbonyl peak range. A combination between filter and detector efficiency range can be selected to assure the proper range selection. The detectors (6.4, 7.7 and 7.8) should be preferably solid state for all applications since they present acceptable efficiency within the carbonyl (C=O) range. Photomultiplier detectors can also be used, preferably for laboratory measurement systems. The percentile measurements should be preferably performed using single or double beam. When using single beam, FIG. 6, the measurement system has to be pre-calibrated for the whole mixture percentile range. Therefore when the sample is introduced in the sample holder, the data processing unit (6.5) compares the intensity of the absorption signal in the carbonyl (C=O) range with calibration data, to mathematically determine the sample mixture percentile. In double beam measurement systems, FIG. 7, the main beam should be preferably filtered by means of an interference or absorption filter (7.2), split into two beams by means of a beam splitter (7.2) and redirected by an appropriate mirror (7.4). A known percentile mixture is placed in the reference beam (7.5) and the unknown mixture is placed in the sample beam (7.6). In this case a comparison between the two readings is supplied to the data processing unity (7.9) which mathematically determines the mixture percentile of the sample.

Equivalent alterations and modifications will occur to others skilled in the art upon the reading and understanding of this specification. The present invention includes all such equivalent alterations and modifications and is limited only by the scope of the following claims.

The invention claimed is:

1. A method for measuring biodiesel concentration in a biodiesel diesel oil mixture which comprises the use of mid infrared radiation absorption measurement in the range from 2000 to 909.09 cm−1 (5000 to 11000 nm).

2. A method as recited in claim 1, wherein the mid infrared radiation is in the range from 1870 to 1600 $cm^{-1}$ (5347.6 to 6250.0 nm) which corresponds to the Carbonyl group peak (C=O), connected to the stretching vibration of ester groups.

3. A method as recited in claim 2, wherein the Carbonyl group peak appears only in biodiesel absorption spectra being strongly independent of synthesis route and raw material source.

4. A method as recited in claim 1, wherein measurement for biodiesel concentration can be performed in the whole range, from 0 to 100% biodiesel in a biodiesel-diesel oil mixture.

5. A method as recited in claim 4, wherein both intensity and area of the carbonyl peak (C=O) present a power law dependence with the concentration of biodiesel in the biodiesel-diesel oil mixture.

6. A method as recited in claim 1, wherein measurement for biodiesel concentration can be performed in the laboratory systems, in the field systems and embarked systems.

7. A method as recited in claim 6, wherein the said embarked systems are able to provide data to adjust performance in explosion engines.

8. A method as recited in claim 6, wherein the measurements can be performed by any infrared spectrometer operating in the range from 2000 to 909.09 cm−1 (5000 to 11000 nm), which includes the carbonyl peak range.

9. A method as recited in claim 8, wherein the said spectrometers can perform measurements using a single or double beam.

* * * * *